United States Patent
Phull et al.

(10) Patent No.: US 8,993,789 B2
(45) Date of Patent: Mar. 31, 2015

(54) PROCESS FOR PREPARING ZANAMIVIR AND INTERMEDIATES FOR USE IN THE PROCESS

(75) Inventors: Manjinder Singh Phull, Maharashtra (IN); Rajendra Narayanrao Kankan, Maharashtra (IN); Dharmaraj Ramachandra Rao, Maharashtra (IN); Ashwini Amol Sawant, Maharashtra (IN); Sanoj Thoppil, Maharashtra (IN)

(73) Assignee: Cipla Limited, Mumbai (IN)

( * ) Notice: Subject to any disclaimer, the term of this patent is extended or adjusted under 35 U.S.C. 154(b) by 885 days.

(21) Appl. No.: 13/130,692

(22) PCT Filed: Nov. 24, 2009

(86) PCT No.: PCT/GB2009/002744
§ 371 (c)(1),
(2), (4) Date: Jul. 8, 2011

(87) PCT Pub. No.: WO2010/061182
PCT Pub. Date: Jun. 3, 2010

(65) Prior Publication Data
US 2011/0257418 A1    Oct. 20, 2011

(30) Foreign Application Priority Data
Nov. 28, 2008 (IN) .................. 2502/MUM/2008

(51) Int. Cl.
C07D 309/14    (2006.01)
C07D 309/28    (2006.01)
(52) U.S. Cl.
CPC .................................. C07D 309/28 (2013.01)
USPC ...................................................... 549/424
(58) Field of Classification Search
CPC .......................... C07D 309/14; C07D 309/28
USPC ........................................................ 549/424
See application file for complete search history.

(56) References Cited

FOREIGN PATENT DOCUMENTS

| | | | |
|---|---|---|---|
| AU | 9351088 B | 4/1994 | |
| EP | 0539204 A1 | 4/1993 | |
| EP | 0526543 B1 | 12/1997 | |
| EP | 0823428 A2 | 2/1998 | |
| EP | 0623121 B1 | 5/1998 | |
| WO | 9116320 A1 | 10/1991 | |
| WO | 9407885 A1 | 4/1994 | |
| WO | WO94/07885 | * | 4/1994 |
| WO | 2010061182 A2 | 6/2010 | |
| WO | 2010061182 A3 | 6/2010 | |

OTHER PUBLICATIONS

Foreign communication from the priority application—International Search Report and Written Opinion, PCT/GB2009/002744, May 26, 2010, 18 pages.
Johnson, Douglas S., et al., "Neuraminidase inhibitors for influenza: oseltamivir phosphate (Tamiflu®) and zanamivir (Relenza®)," The Art of Drug Synthesis, chapt. 7, 2007, pp. 95-114, John Wiley & Sons, Inc, XP-002571327.
Smith, P. W., et al., "Synthesis and influenza virus sialidase inhibitory activity of analogues of 4-guanidino-Neu5Ac2en (GG167) with modified 5-substituents," European Journal of Medicinal Chemistry, 1996, vol. 31, pp. 143-150, Elsevier, Paris.
Foreign communication from the priority application—International Preliminary Report on Patentability, PCT/GB2009/002744, May 31, 2011, 10 pages.

* cited by examiner

*Primary Examiner* — T. Victor Oh
(74) *Attorney, Agent, or Firm* — Rodney B. Carroll; Conley Rose, P.C.

(57) ABSTRACT

The present invention provides a process for preparing methyl 5-acetamido-4-amino-6-(1,2,3-triacetoxypropyl)-5,6-dihydro-4H-pyran-2-carboxylate (V), which process comprises reducing methyl 5-acetamido-4-azido-6-(1,2,3-triacetoxypropyl)-5,6-dihydro-4H-pyran-2-carboxylate (IV) in the presence of a reducing agent selected from the group consisting of lithium aluminum hydride, sodium borohydride, zinc/ammonium chloride, zinc-ferric chloride and ferric chloride/sodium iodide. The present invention also provides compounds of formula (VIII) and (IX) which may be used in the synthesis of zanamivir. The present invention also provides processes for preparing compounds (VIII) and (IX) and processes involving their use, including in the synthesis of zanamivir.

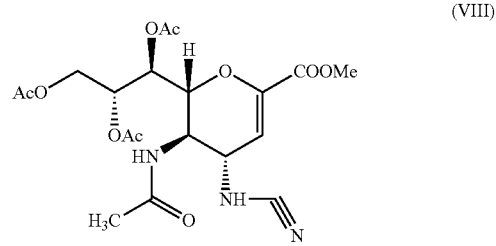

(VIII)

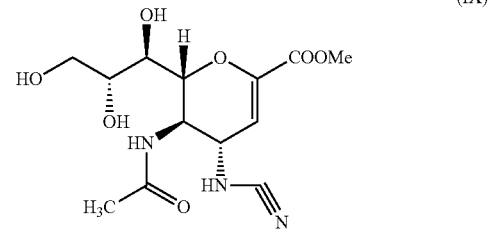

(IX)

17 Claims, No Drawings

US 8,993,789 B2
                  1                                                              2
PROCESS FOR PREPARING ZANAMIVIR           prophylaxis of both Influenza virus A and Influenza virus B.
AND INTERMEDIATES FOR USE IN THE          Chemically, zanamivir is 5-(acetylamino)-4-[(aminoimi-
           PROCESS                        nomethyl)amino]-2,6-anhydro-3,4,5-trideoxy-D-glycero-D-
                                          galacto-non-2-enonic acid (Formula I), and is represented by
    CROSS-REFERENCE TO RELATED            the following structure:
         APPLICATIONS This application is a filing under 35 U.S.C. 371 of International Application No. PCT/GB2009/002744 filed Nov. 24, 2009, entitled "Process for Preparing Zanamivir and Intermediates for Use in the Process," claiming priority of Indian Patent Application No. 2502/MUM/2008 filed Nov. 28, 2008, which applications are incorporated by reference herein in their entirety.

FIELD OF INVENTION

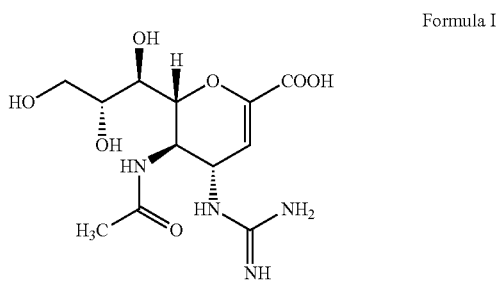 [SMILES: CC(=O)N[C@H]1[C@H]([C@H](O)[C@H](O)CO)OC(C(=O)O)=C[C@@H]1NC(=N)N]

Formula I

The present invention relates to an improved process for the preparation of a neuraminidase inhibitor. More particularly, the present invention relates to a process for the preparation of zanamivir and to novel intermediates for use in the process.

BACKGROUND OF THE INVENTION

Zanamivir is the first neuraminidase inhibitor to be developed commercially, and it is used in the treatment of and Zanamivir binds to the conserved region of influenza neuraminidase enzyme, which mainly catalyzes the cleavage of terminal sialic acid attached to glycolipids and glycoproteins.

The process for preparation of zanamivir was first described in EP 0526543. The synthetic method employed in the patent is depicted in the following reaction Scheme 1:

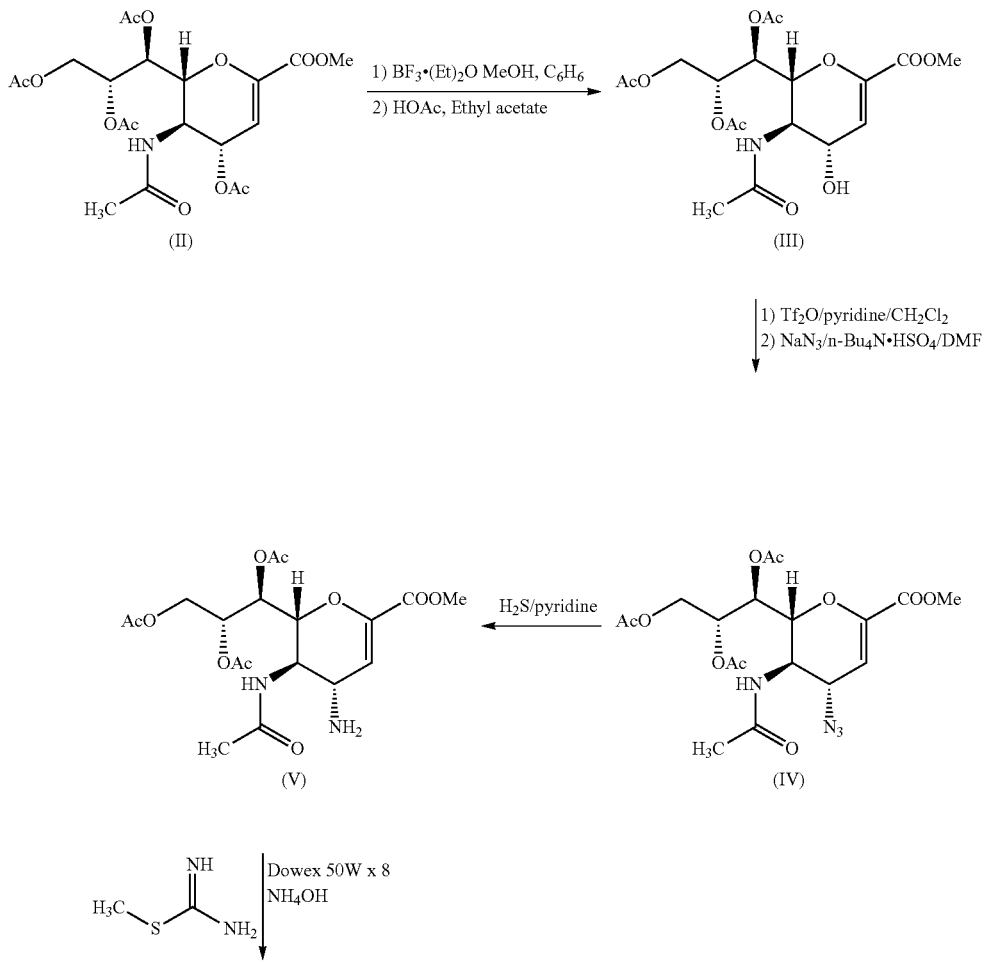

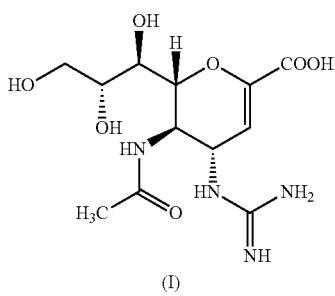

(I)

wherein, selective deacetylation of methyl 5-acetamido-4-acetoxy-6-(1,2,3-triacetoxypropyl)-5,6-dihydro-4H-pyran-2-carboxylate (II) with boron trifluoride ethearate gives methyl 5-acetamido-4-hydroxy-6-(1,2,3-triacetoxypropyl)-5,6-dihydro-4H-pyran-2-carboxylate (III), which on further treatment with trifluoromethanesulfonic anhydride and sodium azide gives methyl 5-acetamido-4-azido-6-(1,2,3-triacetoxypropyl)-5,6-dihydro-4H-pyran-2-carboxylate (IV). The reduction of intermediate compound (IV) with hydrogen sulphide in pyridine affords the corresponding methyl 5-acetamido-4-amino-6-(1,2,3-triacetoxypropyl)-5,6-dihydro-4H-pyran-2-carboxylate intermediate (V), which is finally condensed with S-methylisothiourea in water and saponified through Dowex 50 W×8 in aqueous ammonium hydroxide to yield zanamivir (I). The problems associated with the disclosed process are that even on passing hydrogen sulphide gas for around 16 hours, there is no complete reduction of the 4-azido intermediate into the 4-amino compound. Also, due to the excessive use of the gas, there is a risk of undesired reduction of the 2,3-double bond along with the 4-azido group. The over-reduction leads to formation of undesired products which need additional purification procedures in order to separate the undesired products.

WO 1994/07885 discloses a process for preparing zanamivir, as given in Scheme 2 below, by treating 5-acetamido-4-amino-6-(1,2,3-trihydroxypropyl)-5,6-dihydro-4H-pyran-2-carboxylic acid (VI), obtained from WO 1991/16320, with cyanogen bromide in the presence of sodium acetate to yield 4-cyanoamide derivative (VII) which is further reacted with ammonium formate and ammonia.

Scheme 2

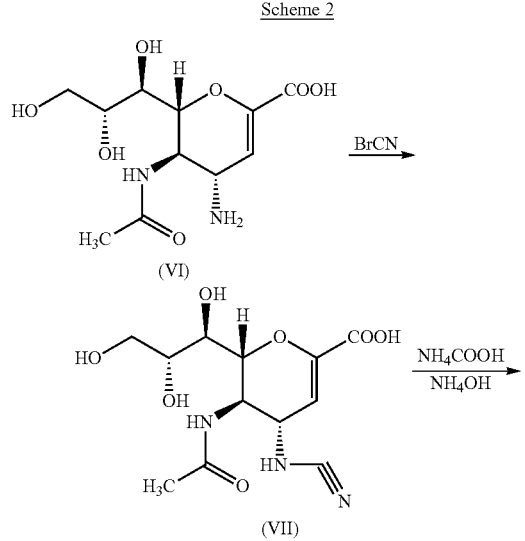

-continued

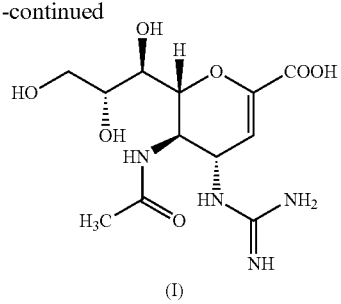

(I)

AU 672634 discloses the synthesis of zanamivir by reacting the 5-acetamido-4-amino-6-(1,2,3-trihydroxypropyl)-5,6-dihydro-4H-pyran-2-carboxylic acid (VI) with pyrazole-1H-carboxamidine.

EP 0539204 also discloses the preparation of zanamivir by treating cyano derivative (VII) with an amine derivative or treating 4-amino compound (VI) with a carbamimidic compound.

EP 0623121 discloses the use of a Lindlar catalyst (lead doped palladium catalyst) for the conversion of the methyl 5-acetamido-4-azido-2,3-didehydro-2,3,4,5-tetradeoxy-D-glycero-D-galacto-2-nonulopyranosidonate to its methyl 5-acetamido-4-amino-2,3-didehydro-2,3,4,5-tetradeoxy-D-glycero-D-galacto-2-nonulopyranosidonate form. It has been found that recovery of the Lindlar catalyst from the reactant solution requires an expensive procedure, thus making the process expensive. Also, this catalyst has a short lifetime due to poisoning.

One of the intermediates for use in the synthesis of zanamivir is the compound of formula (VI), the synthesis of which has previously been described in the above-mentioned patents either by reducing the azido precursor with a Lindlar catalyst or using hydrogen sulphide gas. These processes generate a lot of undesired impurities due to the harsh reaction conditions which further affect the purity and yield of the product. Hence, there is a need for an alternate process for the synthesis of the compound (VI).

The problems associated with the prior art processes involve the use of a costly catalyst, expensive recovery procedures and high reaction time. Hence, in order to overcome these problems, there is need for an improved or alternate process for preparation of zanamivir that is simple, economical, eco-friendly and industrially scaleable.

SUMMARY OF THE INVENTION

According to a first aspect of the present invention, there is provided a process for preparing methyl 5-acetamido-4-amino-6-(1,2,3-triacetoxypropyl)-5,6-dihydro-4H-pyran-2-carboxylate (V), which process comprises reducing methyl 5-acetamido-4-azido-6-(1,2,3-triacetoxypropyl)-5,6-dihydro-4H-pyran-2-carboxylate (IV) in the presence of a reducing agent selected from the group consisting of lithium aluminium hydride, sodium borohydride, zinc/ammonium chloride, zinc-ferric chloride and ferric chloride/sodium iodide.

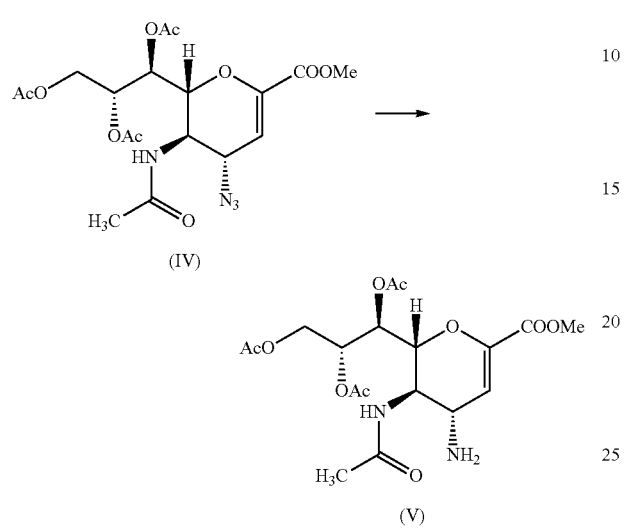

(IV)

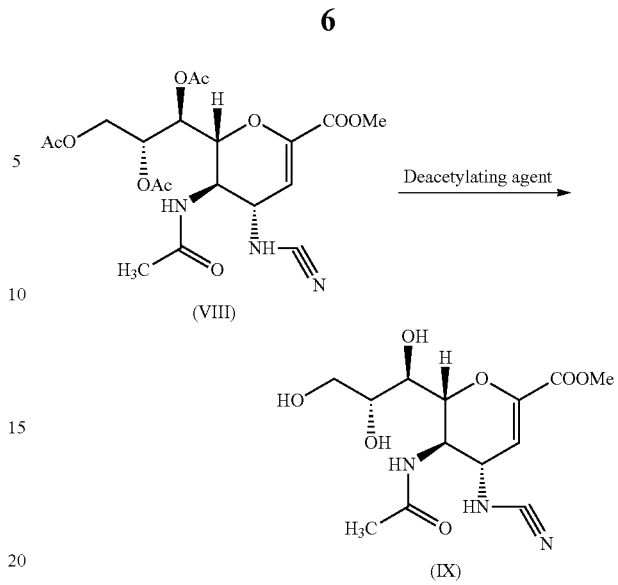

(VIII)

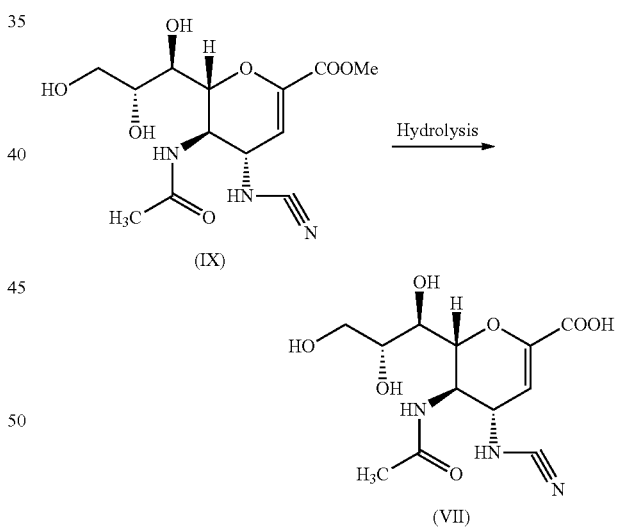

(IX)

In an embodiment, the deacetylating agent is selected from the group consisting of methanol/iodine, methanol/water, sodium t-butoxide, potassium carbonate, sodium hydroxide, and sodium methoxide. Preferably, the deacetylating agent is sodium methoxide.

In an embodiment, compound (VIII) has been prepared according to the process described above.

According to another aspect of the present invention, there is provided a process for preparing a compound of formula (VII), which process comprises hydrolysing the ester group of a compound of formula (IX).

(V)

In an embodiment, the reducing agent is zinc/ammonium chloride, preferably zinc dust/ammonium chloride.

According to another aspect of the present invention, there is provided a process for preparing a compound of formula (VIII), which process comprises reacting a compound of formula (V) with a cyanogen halide.

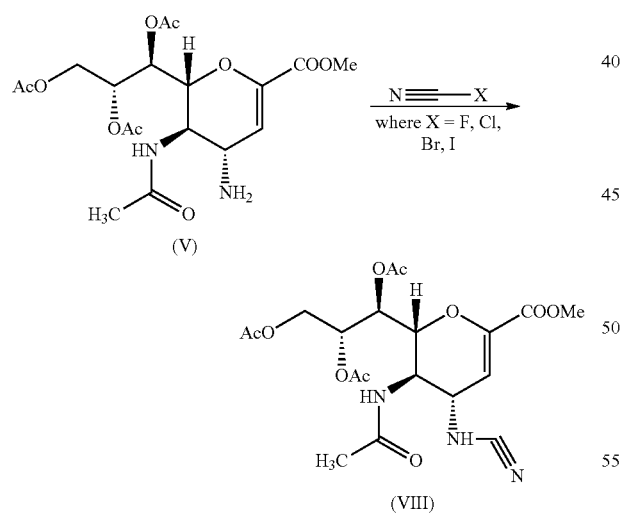

(V)

(VIII)

In an embodiment, the cyanogen halide is cyanogen bromide.

In an embodiment, the compound of formula (V) has been prepared according to the process described above.

According to another aspect of the present invention, there is provided a process for preparing a compound of formula (IX), which process comprises deacetylation of a compound of formula (VIII).

(IX)

(VII)

In an embodiment, the hydrolysis takes place in the presence of an organic or inorganic base. The organic base may be selected from the group consisting of pyridine, dimethylamine, trimethylamine and sodium ethoxide. The inorganic base may be selected from the group consisting of sodium carbonate, potassium carbonate, magnesium carbonate, calcium carbonate, sodium bicarbonate, and potassium bicarbonate.

In an embodiment, compound (IX) has been prepared according to the process described above.

According to another aspect of the present invention, there is provided a process for preparing zanamivir of formula (I), which process comprises preparing a compound of formula (VII) according to the process described above, and reacting the compound of formula (VII) with ammonium formate in presence of ammonia.

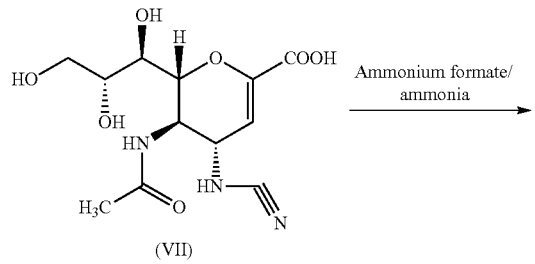

(VII)

Ammonium formate/ ammonia →

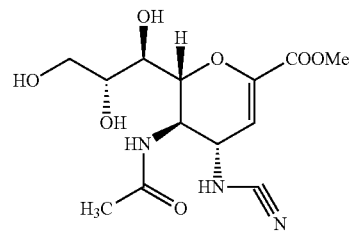

(IX)

According to another aspect of the present invention, there is provided the use of methyl 5-acetamido-4-cyanamido-6-(1,2,3-triacetoxypropyl)-5,6-dihydro-4H-pyran-2-carboxylate of formula (VIII) in the synthesis of zanamivir.

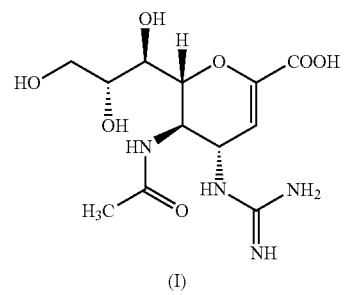

(I)

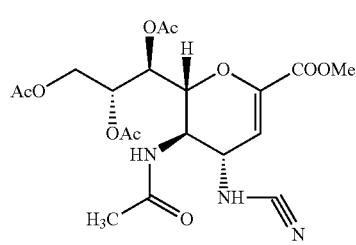

(VIII)

According to another aspect of the present invention, there is provided the use of methyl 5-acetamido-4-cyanamido-6-(1,2,3-trihydroxypropyl)-5,6-dihydro-4H-pyran-2-carboxylate of formula (IX) in the synthesis of zanamivir.

In an embodiment, the ammonia is in the form of gaseous ammonia, liquid ammonia, or aqueous ammonia. Suitably, the reaction of the compound (VII) to form zanamivir is carried out at a high temperature ranging from about 80° C. to about 100° C.

Typically, the zanamivir is isolated as a solid. The crude solid may be purified. For example, the process may further comprise recrystallising the crude zanamivir. In an embodiment, the solid product may be purified with water, an alcoholic solvent or mixtures thereof. The purified zanamivir is typically produced having a high purity, for example a purity of 99.5% or higher, as determined by HPLC.

According to another aspect of the present invention, there is provided methyl 5-acetamido-4-cyanamido-6-(1,2,3-triacetoxypropyl)-5,6-dihydro-4H-pyran-2-carboxylate of formula (VIII).

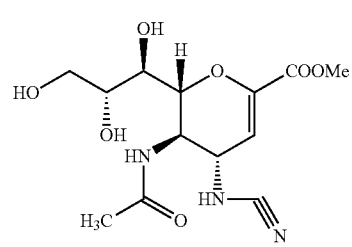

(IX)

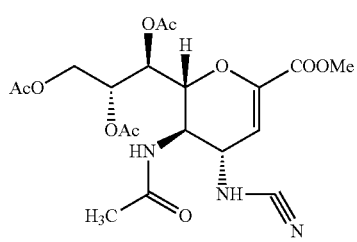

(VIII)

According to another aspect of the present invention, there is provided methyl 5-acetamido-4-cyanamido-6-(1,2,3-trihydroxypropyl)-5,6-dihydro-4H-pyran-2-carboxylate of formula (IX).

According to another aspect of the present invention, there is provided zanamivir having purity greater than or equal to 99.5%.

According to another aspect of the present invention, there is provided zanamivir prepared according to a process described above.

According to another aspect of the present invention, there is provided a pharmaceutical composition comprising zanamivir prepared according to a process described above together with one or more excipients.

According to another aspect of the present invention, there is provided the use of zanamivir prepared according to a process described above in medicine.

According to another aspect of the present invention, there is provided zanamivir prepared according to a process described above for use in the treatment or prophylaxis of Influenza virus A or Influenza virus B.

DETAILED DESCRIPTION OF THE INVENTION

The invention will now be described in detail in connection with certain preferred and optional embodiments, so that various aspects thereof may be more fully understood and appreciated.

In an embodiment, the present invention provides a process for preparing methyl 5-acetamido-4-amino-6-(1,2,3-triacetoxypropyl)-5,6-dihydro-4H-pyran-2-carboxylate (V), as depicted in Scheme 3 below.

Scheme 3

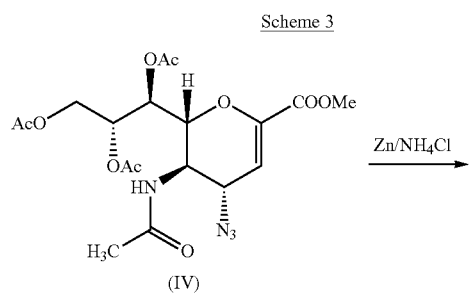

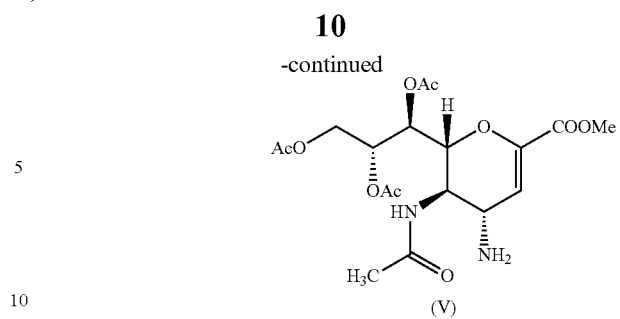

The reduction of methyl 5-acetamido-4-azido-6-(1,2,3-triacetoxypropyl)-5,6-dihydro-4H-pyran-2-carboxylate (which may be obtained by following the process mentioned in EP0526543) (IV) with a reducing agent selected from the group consisting of lithium aluminium hydride, sodium borohydride, zinc/ammonium chloride, zinc-ferric chloride and ferric chloride/sodium iodide, preferably zinc dust/ammonium chloride, leads to formation of the compound of formula (V).

The reduction of the azide group to the corresponding amine group occurs under mild conditions and may be carried out at room temperature (for example 25° C.-35° C.) due to the use of the milder reducing agent.

Also, an important feature of, for example, zinc is that the process requires shorter time for completion as compared to the prior art processes.

Further, the use of, for example, zinc does not cause undesired reduction of the 2,3-double bond of the ring thus preventing formation of side-products.

In another embodiment, the present invention provides a process for preparing zanamivir which process involves the use of novel intermediates VIII and IX, as depicted below in Scheme 4.

Scheme 4

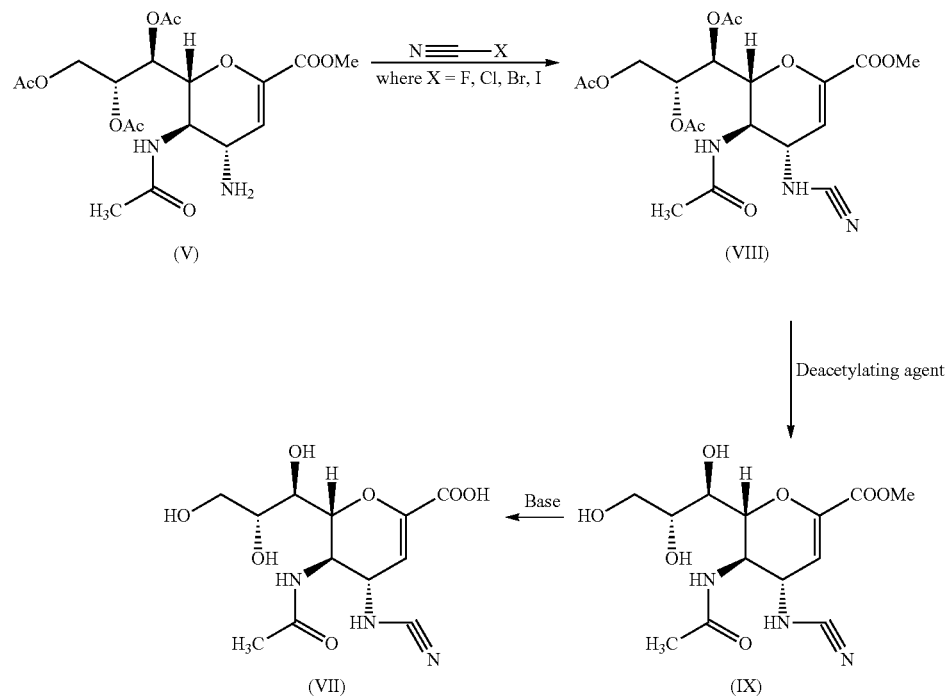

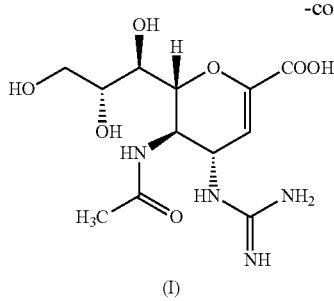

(I)

Accordingly, in an embodiment, the present invention provides a process for preparing zanamivir of formula I, which process comprises:

A] treating a compound of formula (V) with a cyanogen halide which may be selected from cyanogen fluoride, cyanogen chloride, cyanogen bromide or cyanogen iodide to obtain methyl 5-acetamido-4-cyanamido-6-(1,2,3-triacetoxypropyl)-5,6-dihydro-4H-pyran-2-carboxylate (VIII);

B] deacetylating the intermediate (VIII) to obtain methyl 5-acetamido-4-cyanamido-6-(1,2,3-trihydroxypropyl)-5,6-dihydro-4H-pyran-2-carboxylate (IX). The reaction may be carried out in the presence of a deacetylating agent which may be selected from the group consisting of methanol/iodine, methanol/water, sodium t-butoxide, potassium carbonate, sodium hydroxide, or sodium methoxide;

C] hydrolyzing the compound (IX) in a basic medium to obtain 5-acetamido-4-cyanamido-6-(1,2,3-trihydroxypropyl)-5,6-dihydro-4H-pyran-2-carboxylic acid of formula (VII). The base used in the reaction may be organic or inorganic. The organic base may be selected from the group consisting of pyridine, dimethylamine, trimethylamine and sodium ethoxide. The inorganic base may be selected from the group consisting of sodium carbonate, potassium carbonate, magnesium carbonate, calcium carbonate, sodium bicarbonate and potassium bicarbonate; and D] reacting the compound (VII) with ammonium formate in the presence of ammonia which may be in the form of gaseous ammonia, liquid ammonia or aqueous ammonia and at a high temperature, for example ranging from 80° C. to 100° C., to obtain zanamivir (I).

The solid product may optionally be purified with water, an alcoholic solvent or mixtures thereof to obtain highly pure zanamivir having HPLC purity of 99.5% or higher.

Typically, the process for preparation of zanamivir (I) of the present invention is depicted in Scheme 5 below:

Scheme 5

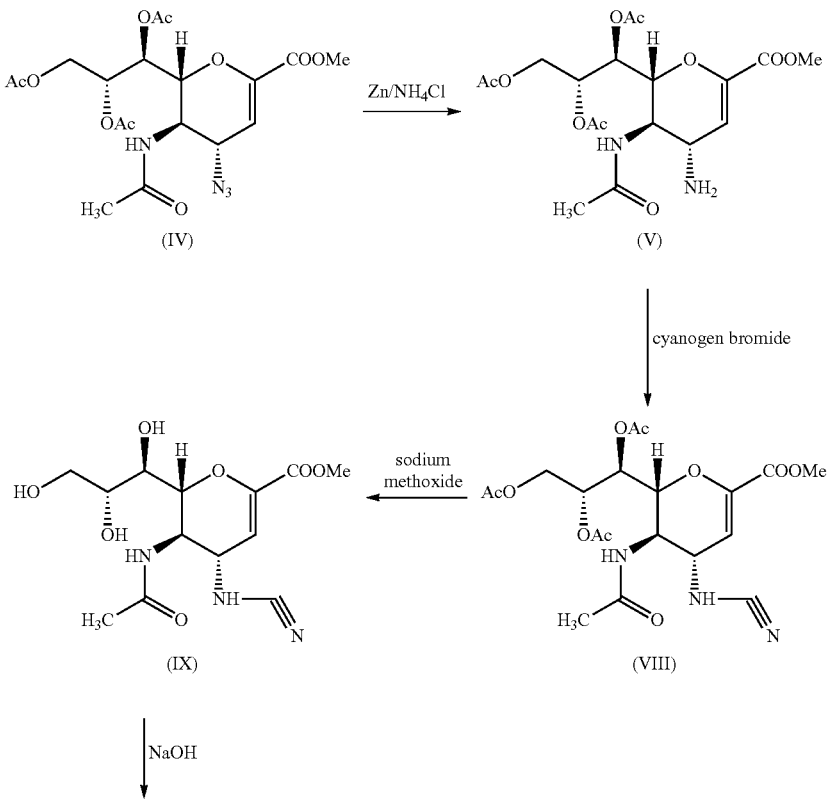

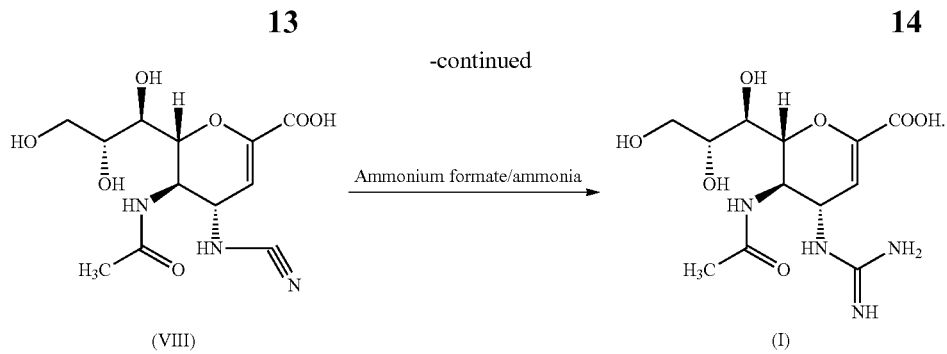

In still another embodiment, the process for preparing zanamivir is carried out by isolating the intermediates obtained in the preceding steps.

In an embodiment, the process of the present invention involves the use of zinc/ammonium chloride as the reducing agent which is a cheap and easily recoverable catalyst. Further, with the use of this catalyst, the time required for completion of reaction is shorter as compared to the prior art processes wherein about 4 to 16 hours are required for reduction to take place. The process of the present invention is simple, economical, eco-friendly, and industrially scaleable.

EXAMPLES

The following examples, which include preferred embodiments, will serve to illustrate the practice of this invention, it being understood that the particulars shown are by way of example and for purpose of illustrative discussion of preferred embodiments of the invention.

Step A: Preparation of methyl 5-acetamido-4-amino-6-(1,2,3-triacetoxypropyl)-5,6-dihydro-4H-pyran-2-carboxylate—compound (IV) to compound (V)

To a reaction vessel, 55 g of methyl 5-acetamido-4-azido-6-(1,2,3-triacetoxypropyl)-5,6-dihydro-4H-pyran-2-carboxylate, 500 ml of denatured alcohol and 100 ml of water was added under stirring at room temperature. To the reaction mass 14 g ammonium chloride and 18 g zinc dust was added. The reaction mixture was stirred at 20° C.-30° C. for 30 minutes. On completion of reaction, the reaction mass was cooled to 10° C. and then filtered through hyflo. The filtrate was concentrated under vacuum to obtain a solid product which was then dissolved in about 200 ml of methylene dichloride. The organic layer was filtered and concentrated to yield 52 g of solid title compound, dried under vacuum (yield—94%, HPLC purity—96%).

Step B: Preparation of methyl 5-acetamido-4-cyanamido-6-(1,2,3-triacetoxypropyl)-5,6-dihydro-4H-pyran-2-carboxylate—compound (V) to compound (VIII)

10 g of compound, obtained from step A, was stirred with 70 ml methanol. The resulting reaction mass was cooled to 15° C. and then sodium acetate (4.2 g) was added. A solution of cyanogen bromide (3.0 g) dissolved in 30 ml methanol was added dropwise and stirred at 15° C. After completion of addition, reaction mass was stirred at 20° C. for 1 hour and used as such in the next stage of synthesis.

Step C: Preparation of methyl 5-acetamido-4-cyanamido-6-(1,2,3-trihydroxypropyl)-5,6-dihydro-4H-pyran-2-carboxylate—compound (VIII) to compound (IX)

10.5 g of reaction mass from step B containing methanol was chilled to about 15° C. and then sodium methoxide (3.1 g) was added at 10° C.-15° C. The reaction mass was stirred for 30 min at 20° C. and was monitored. This reaction mass (7.6 g) was used in the next step of synthesis.

Step D: Preparation of 5-acetamido-4-cyanamido-6-(1,2,3-trihydroxypropyl)-5,6-dihydro-4H-pyran-2-carboxylic acid—compound (IX) to compound (VII)

A solution of reaction mass (7.6 g), from step C, in methanol was cooled to 15° C. To this a solution of sodium hydroxide (0.9 g) in 30 ml water was added at 15° C. and then stirred at 25° C. for an hour. After completion of reaction, 50 ml water was charged and pH of the reaction mass was adjusted with amberlite cation resin to pH 6.5-7. The resin was filtered, washed with deionised water and the filtrate was concentrated below 50° C. to obtain a solid residue (7.3 g).

Step E: Preparation of Zanamivir

In a reaction vessel, 7.3 g of the solid residue, from step D, was taken and to it 7.3 g of ammonium formate along with 140 ml ammonia added at 25° C.-30° C. The reaction mass was heated to 90° C. for 3 hrs. 0.7 g of charcoal was added to this reaction mass and content was stirred for about 1 hr. Then the mass was cooled to 20° C.-25° C. and filtered. The filtrate was concentrated at 60° C. under vacuum to obtain residue in which 100 ml of methanol was added and stirred. The resulting solid was filtered and dried under vacuum to yield 5.0 g of the title compound (yield—69%, HPLC purity—85%).

Step F: Purification of Zanamivir

Crude zanamivir (5 g), from earlier step, was stirred with 50 ml of water and heated to 90° C. to get suspension. To it 4 g charcoal was added and filtered hot through hyflo to get a clear solution. To the clear filtrate 15 ml of isopropyl alcohol was added dropwise. The solid thus obtained was filtered, washed with isopropyl alcohol and dried under vacuum at 60° C. to obtain 2.5 g of pure zanamivir (HPLC purity—99.5%).

It will be appreciated that the invention may be modified within the scope of the appended claims.

The invention claimed is:

1. Methyl 5-acetamido-4-cyanamido-6-(1,2,3-triacetoxypropyl)-5,6-dihydro-4H-pyran-2-carboxylate of formula (VIII)

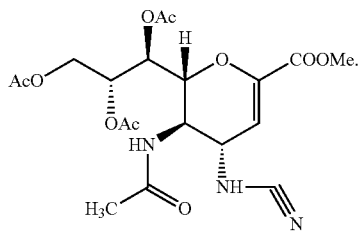

2. Methyl 5-acetamido-4-cyanamido-6-(1,2,3-trihydroxypropyl)-5,6-dihydro-4H-pyran-2-carboxylate of formula (IX)

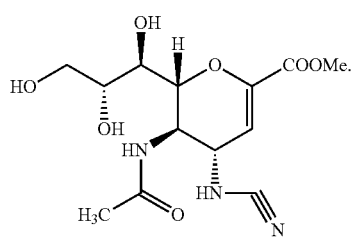

3. A method of synthesizing zanamivir comprising deacetylating the methyl 5-acetamido-4-cyanamido-6-(1,2,3-triacetoxypropyl)-5,6-dihydro-4H-pyran-2-carboxylate of formula (VIII) according to claim 1

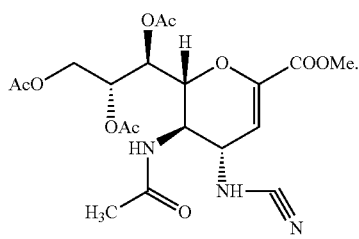

4. A method of synthesizing zanamivir comprising hydrolyzing the methyl 5-acetamido-4-cyanamido-6-(1,2,3-trihydroxypropyl)-5,6-dihydro-4H-pyran-2-carboxylate of formula (IX) according to claim 2

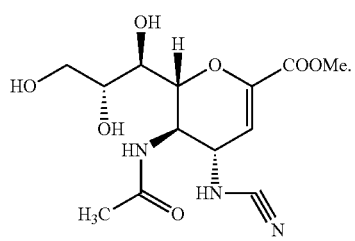

5. A process for preparing the compound of formula (VIII) according to claim 1, which process comprises reacting a compound of formula (V), methyl 5-acetamido-4-amino-6-(1,2,3-triacetoxypropyl)-5,6-dihydro-4H-pyran-2-carboxylate, with a cyanogen halide of formula N≡C—X, wherein X is fluoro, chloro, bromo or iodo

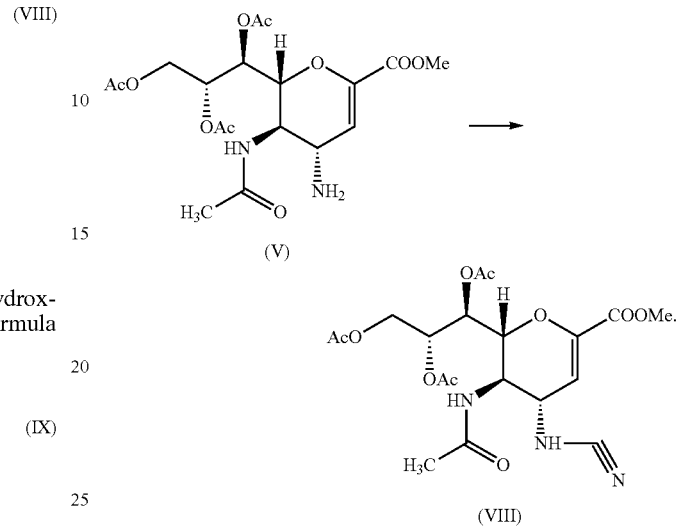

6. The process according to claim 5, wherein the compound of formula (V), methyl 5-acetamido-4-amino-6-(1,2,3-triacetoxypropyl)-5,6-dihydro-4H-pyran-2-carboxylate, is prepared by reducing a compound of formula (IV), methyl-5-acetamido-4-azido-6-(1,2,3-triacetoxypropyl)-5,6-dihydro-4H-pyran-2-carboxylate, in the presence of a reducing agent selected from the group consisting of lithium aluminium hydride, sodium borohydride, zinc/ammonium chloride, zinc-ferric chloride and ferric chloride/sodium iodide

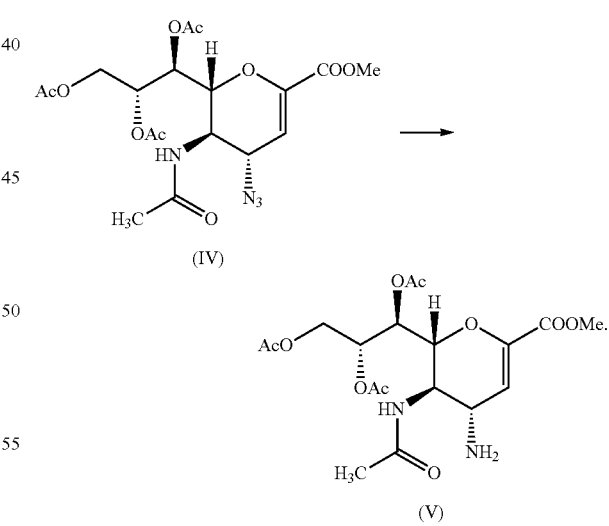

7. The process according to claim 6, wherein the reducing agent is zinc/ammonium chloride.

8. The process according to claim 5, wherein the cyanogen halide is cyanogen bromide.

9. A process for preparing the compound of formula (IX) according to claim 2 comprising deacetylating a compound of formula (VIII)

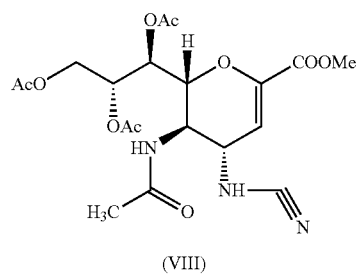

(VIII)

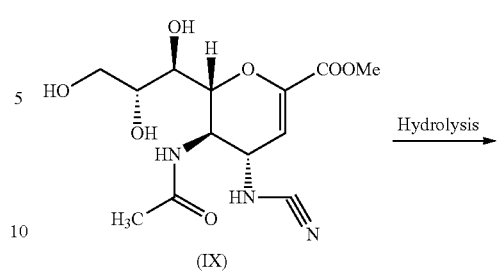

(IX)

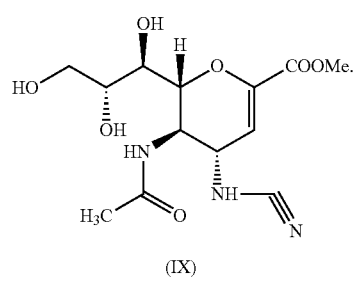

(IX)

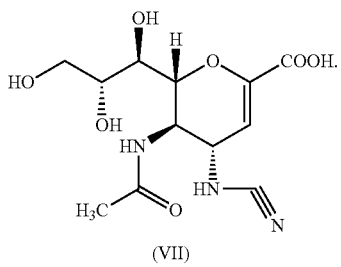

(VII)

10. The process according to claim 9, wherein deacetylating a compound of formula (VIII) occurs in the presence of deacetylating agent, wherein the deacetylating agent is selected from the group consisting of methanol/iodine, methanol/water, sodium t-butoxide, potassium carbonate, sodium hydroxide, and sodium methoxide.

11. The process according to claim 9, wherein the compound of formula (VIII) has been prepared by reacting a compound of formula (V) with a cyanogen halide of formula N≡C—X, wherein X is fluoro, chloro, bromo or iodo

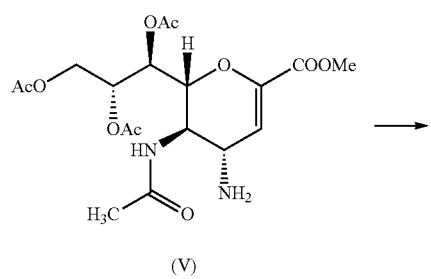

(V)

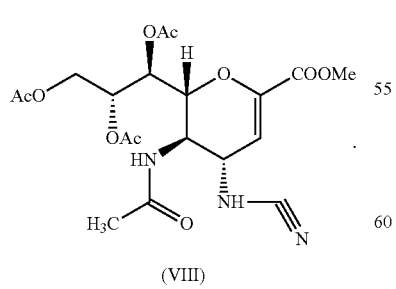

(VIII)

12. A process for preparing a compound of formula (VII), which process comprises hydrolysing the compound of formula (IX) according to claim 2

13. The process according to claim 12, wherein the hydrolysis takes place in the presence of an organic or inorganic base.

14. The process according to claim 12, wherein the base is selected from the group consisting of pyridine, dimethylamine, trimethylamine, sodium ethoxide, sodium carbonate, potassium carbonate, magnesium carbonate, calcium carbonate, sodium bicarbonate and potassium bicarbonate.

15. The process according to claim 12, wherein the compound of formula (IX) has been prepared by deacetylation of a compound of formula (VIII) in the presence of a deacetylating agent

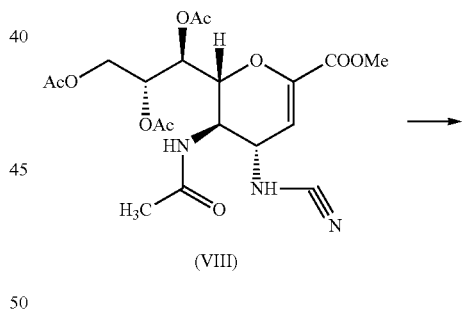

(VIII)

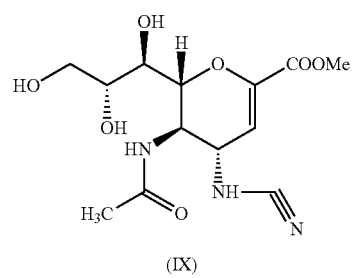

(IX)

wherein the deacetylating agent is selected from the group consisting of methanol/iodine, methanol/water, sodium t-butoxide, potassium carbonate, sodium hydroxide, and sodium methoxide.

16. A process for preparing zanamivir, which process comprises preparing a compound of formula (VII) according to claim 12, and reacting the compound of formula (VII) with ammonium formate in the presence of ammonia to obtain zanamivir.

17. The process according to claim 16, further comprising recrystallising the zanamivir.

\* \* \* \* \*